United States Patent [19]
Aida et al.

[11] Patent Number: 5,583,246
[45] Date of Patent: Dec. 10, 1996

[54] LACTONE-MODIFIED ORGANOPOLYSILOXANE COMPOUND AND A PROCESS FOR ITS PREPARATION

[75] Inventors: Haruhiko Aida, Hiratsuka; Noboru Nakai, Isehara; Osamu Isozaki, Yokohama, all of Japan

[73] Assignee: Kansai Paint Company, Limited, Amagasaki, Japan

[21] Appl. No.: 573,545

[22] Filed: Dec. 15, 1995

[30] Foreign Application Priority Data

Dec. 21, 1994 [JP] Japan .................................. 6-318006

[51] Int. Cl.⁶ .................................. C07F 7/18; C07F 7/08
[52] U.S. Cl. .......................................................... 556/437
[58] Field of Search ............................................... 556/437

[56] References Cited

U.S. PATENT DOCUMENTS 3,778,458 12/1973 Morehouse .............................. 556/437
4,783,542 11/1988 Chung ..................................... 556/437
5,385,730  1/1995 Ichinohe ............................... 556/437 X

*Primary Examiner*—Paul F. Shaver
*Attorney, Agent, or Firm*—Armstrong, Westerman, Hattori, McLeland & Naughton

[57] ABSTRACT

The invention provides a lactone-modified organopolysiloxane compound represented by the formula

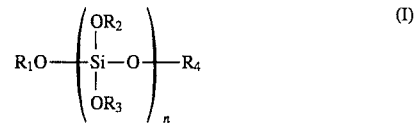

wherein $R_1$, $R_2$, $R_3$ and $R_4$ are the same or different and each represents a methyl group, an ethyl group, a n-propyl group, an isopropyl group or a group represented by the formula

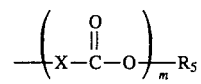

wherein $R_5$ is a methyl group, an ethyl group, a n-propyl group or an isopropyl group, X is a saturated divalent hydrocarbon group having 2 to 14 carbon atoms, and m is an integer of 1 to 3, provided that at least one of $R_1$, $R_2$, $R_3$ and $R_4$ is a group represented by the formula

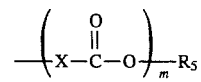

wherein $R_5$, X and m are as defined above, and n is an integer of 1 to 100. The polysiloxane compound of the invention is excellent in compatibility with various organic resins.

4 Claims, 1 Drawing Sheet

LACTONE-MODIFIED ORGANOPOLYSILOXANE COMPOUND AND A PROCESS FOR ITS PREPARATION

The present invention relates to a novel lactone-modified organopolysiloxane compound and a process for the preparation of the compound.

A tetraalkyl silicate or its condensate, i.e. a known organopolysiloxane compound, is used in various fields because of their high resistance to heat and to chemicals. But the compounds have the drawback of use in a limited manner owing to their poor compatibility with organic resins.

In this situation, it is earnestly desired in the industry to develop an organopolysiloxane compound free of such drawback.

An object of the present invention is to provide a novel organopolysiloxane compound which has overcome the drawback.

Another object of the present invention is to provide a novel organopolysiloxane compound which is highly compatible with various organic resins.

Other objects and features of the present invention will become apparent from the following description.

According to the present invention, there is provided a lactone-modified organopolysiloxane compound represented by the formula (I)

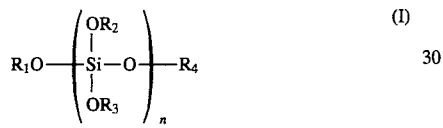

wherein $R_1$, $R_2$, $R_3$ and $R_4$ are the same or different and each represents a methyl group, an ethyl group, a n-propyl group, an isopropyl group or a group represented by the formula

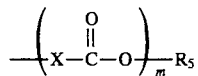

wherein $R_5$ is a methyl group, an ethyl group, a n-propyl group or an isopropyl group, X is a saturated divalent hydrocarbon group having 2 to 14 carbon atoms, and m is an integer of 1 to 3, provided that at least one of $R_1$, $R_2$, $R_3$ and $R_4$ is a group represented by the formula

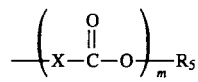

wherein $R_5$, X and m are as defined above, and n is an integer of 1 to 100.

According to the present invention, there is also provided a process for the preparation of the compound.

The inventor of the present invention conducted extensive research to overcome the foregoing prior art drawback and found that when an organopolysiloxane compound is modified with a lactone, there is obtained a novel organopolysiloxane compound having a high compatibility with various organic resins which is free of the drawback is prepared. The present invention has been accomplished based on this novel finding.

The saturated divalent hydrocarbon group of 2 to 14 carbon atoms represented by X in the formula (I) is preferably a straight methylene chain saturated divalent hydrocarbon group of 2 to 10 carbon atoms, or a branched methylene chain saturated divalent hydrocarbon group having some of hydrogen atoms of the methylene chain substituted by a lower alkyl group of 1 to 4 carbon atoms. Specific examples are the groups

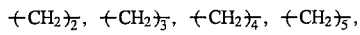

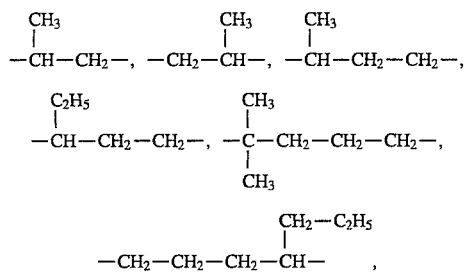

etc. When each of $R_1$, $R_2$, $R_3$, $R_4$ and $R_5$ is a methyl group, an ethyl group, a n-propyl group or an isopropyl group, an ethyl group is the most preferred. Preferably n in the formula (I) is about 2 to about 10.

The lactone-modified organopolysiloxane compound of the formula (I) according to the invention can be suitably prepared by subjecting to ring opening addition reaction:

(i) a silicon compound represented by the formula (II)

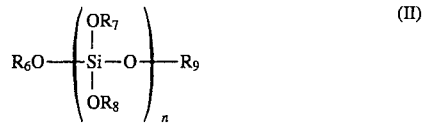

wherein $R_6$, $R_7$, $R_8$ and $R_9$ are the same or different and each is a methyl group, an ethyl group, a n-propyl group or an isopropyl group and n is as defined above, and (ii) a lactone compound represented by the formula (III)

wherein X is as defined above.

Examples of the silicon compound of the formula (II) include a tetraalkyl silicate or its condensate. Suitable examples are monomers to centimers (polymers formed from 100 molecules) (n=1 to 100), preferably approximately dimers to decamers (n=2 to 10), of a tetraalkyl silicate. Specific examples of useful silicon compounds are "COL-COTE ES 40" (trademark, product of COLCOTE CO., LTD., a mixture of monomer to decamer, an average of pentamer, of a tetraethyl silicate), "COLCOTE MS 51" (trademark, product of COLCOTE CO., LTD., a mixture of monomer to decamer, an average of pentamer, of a tetramethyl silicate), etc.

Examples of the lactone compound of the formula (III) are γ-valerolactone, δ-valerolactone, ε-caprolactone, α-methyl-β-propiolactone, β-methyl-β-propiolactone, 3-n-propyl-δ-valerolactone, 6,6-dimethyl-δ-valerolactone, β-propiolactone, γ-butyrolactone, δ-caprolactone, etc. Among them, ε-caprolactone is preferred.

The silicon compound of the formula (II) and the lactone compound of the formula (III) are used in the reaction in such proportions that the molar ratio of the lactone compound relative to the combined amount of the groups $R_6$, $R_7$, $R_8$ and $R_9$ in the silicon compound of the formula (II) is about 0.05 to about 3.0, preferably about 0.1 to about 1.5. If the lactone compound is used in the molar ratio of less than 0.05, the modification effect tends to become insufficient and the compatibility with organic resins would be lowered. On the other hand, the lactone compound used in the molar ratio of more than 3.0 would be likely to impair the resistance to heat and to chemicals which are the characteristics of the silicon compound. Hence it is undesirable to use the lactone compound in a molar ratio outside said range.

The ring opening addition reaction of the silicon compound of the formula (II) with the lactone compound of the formula (III) is preferably conducted in the presence of a catalyst for ring opening addition reaction. Examples of preferred catalysts for ring opening addition reaction are n-butyltin trioctate, dibutyltin dilaurate, dimethyltin dichloride, dibutyltin dichloride, dibutyltin diacetate and like organotin compounds; stannous chloride, stannic chloride and like halogenated tin compounds; organic zirconium compounds; tetrabutyl titanate, tetrabutoxy titanate, tetraethyl titanate and like organic titanium compounds; boron trifluoride, aluminum trichloride, zinc chloride, titanium chloride and like Lewis acids; and tetrabutylammonium fluoride, cesium fluoride, potassium fluoride, rubidium fluoride and like fluoride salts to which catalysts useful in the invention are not limited. These catalysts can be used either alone or in combination.

The amount of the catalyst used in the invention is about 0.01 to about 10% by weight, preferably about 0.02 to about 4.0% by weight, based on the combined amount of the silicon compound and the lactone compound.

The foregoing ring opening addition reaction is suitably conducted in the presence or the absence of a solvent inert to the reaction at a temperature of about 80° to about 200° C., preferably about 100° to about 180° C. The reaction time is generally about 1 to about 20 hours.

Examples of inert solvents which can be used in the reaction are hydrocarbons such as toluene, xylene, hexane, heptane and the like, esters such as ethyl acetate, butyl acetate and the like, ketones such as acetone, methyl ethyl ketone and the like, and halogenated hydrocarbons such as dichloromethane, chloroform and the like. These solvents can be used either alone or in combination. It is undesirable to use a large amount of a solvent which is active to the reaction, such as a hydroxyl-containing solvent, because the modification ratio of the lactone is reduced.

The reaction is carried out, for example, by mixing and heating the silicon compound and the lactone compound or by adding dropwise the lactone compound to the silicon compound. For use, the catalyst may be mixed with the silicon compound or may be mixed with the lactone compound before the dropwise addition.

The lactone-modified organopolysiloxane compound of the present invention is highly compatible with various organic resins. In use, the compound may be mixed with, for example, a hydroxyl-containing resin to give a curable resin composition serving as a coating composition which is capable of forming a tough coating film when heated in the presence of an organotin compound or like catalyst.

In other use, the lactone-modified organopolysiloxane compound of the present invention may be mixed with, for example, a hydroxyl-containing resin, a polyepoxide resin or the like, thereby producing a curable resin composition which has superior low temperature curability and is capable of forming a coating film excellent in properties such as resistance to weather and to acids and the like when heated in the presence of a metal chelate compound as a catalyst.

According to the present invention, a novel lactone-modified organopolysiloxane compound which is highly compatible with organic resins can be obtained. The obtained compound, when mixed with, for example, a hydroxyl-containing resin, is capable of producing a cured product such as a coating film which is superior in properties such as resistance to weather and to acids, etc.

The present invention will be described below in more detail with reference to Preparation Example, Examples, Application Examples and Comparative Application Examples.

Preparation Example 1

| Preparation of hydroxyl-containing resin (1) | |
| --- | --- |
| 2-Hydroxyethyl acrylate | 232 g |
| n-Butyl methacrylate | 618 g |
| Styrene | 150 g |
| Azobisisobutyronitrile | 20 g |

A mixture of the foregoing components was added dropwise to 1,000 g of xylene at 110° C. The mixture was subjected to a reaction for 5 hours, thereby producing an acrylpolyol having a number average molecular weight of 20,000 and an hydroxyl value of 112.

Example 1

Preparation of lactone-modified organopolysiloxane compound (i)

Into a 4-necked flask equipped with a condenser, thermometer, nitrogen inlet tube, stirrer, and dropping funnel were placed 744 g of COLCOTE ES 40 (trademark, product of COLCOTE CO., LTD., a mixture of an average of approximately pentamer of a tetraethyl silicate having an average of about 12 ethoxy groups per molecule, the same hereinafter) and 7 g of n-butyltin trioctate, and the mixture was heated to 140° C. A 684 g quantity (6 mols) of PLACCEL M (trademark, product of DAICEL CHEMICAL INDUSTRIES, ε-caprolactone, the same hereinafter) was added dropwise through a dropping funnel over a period of 3 hours. After 4 hours of stirring, the mixture was cooled, giving a lactone-modified organopolysiloxane compound (i) according to the present invention. The obtained compound was a compound of the formula (I) wherein 6 out of an average of 12 ethoxy groups per molecule were substituted by a group represented by

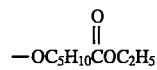

and wherein n is 5. The compound had a number average molecular weight of about 1,600 as determined by gel permeation chromatography.

Example 2

Preparation of lactone-modified organopolysiloxane compound (ii)

Figure 1:
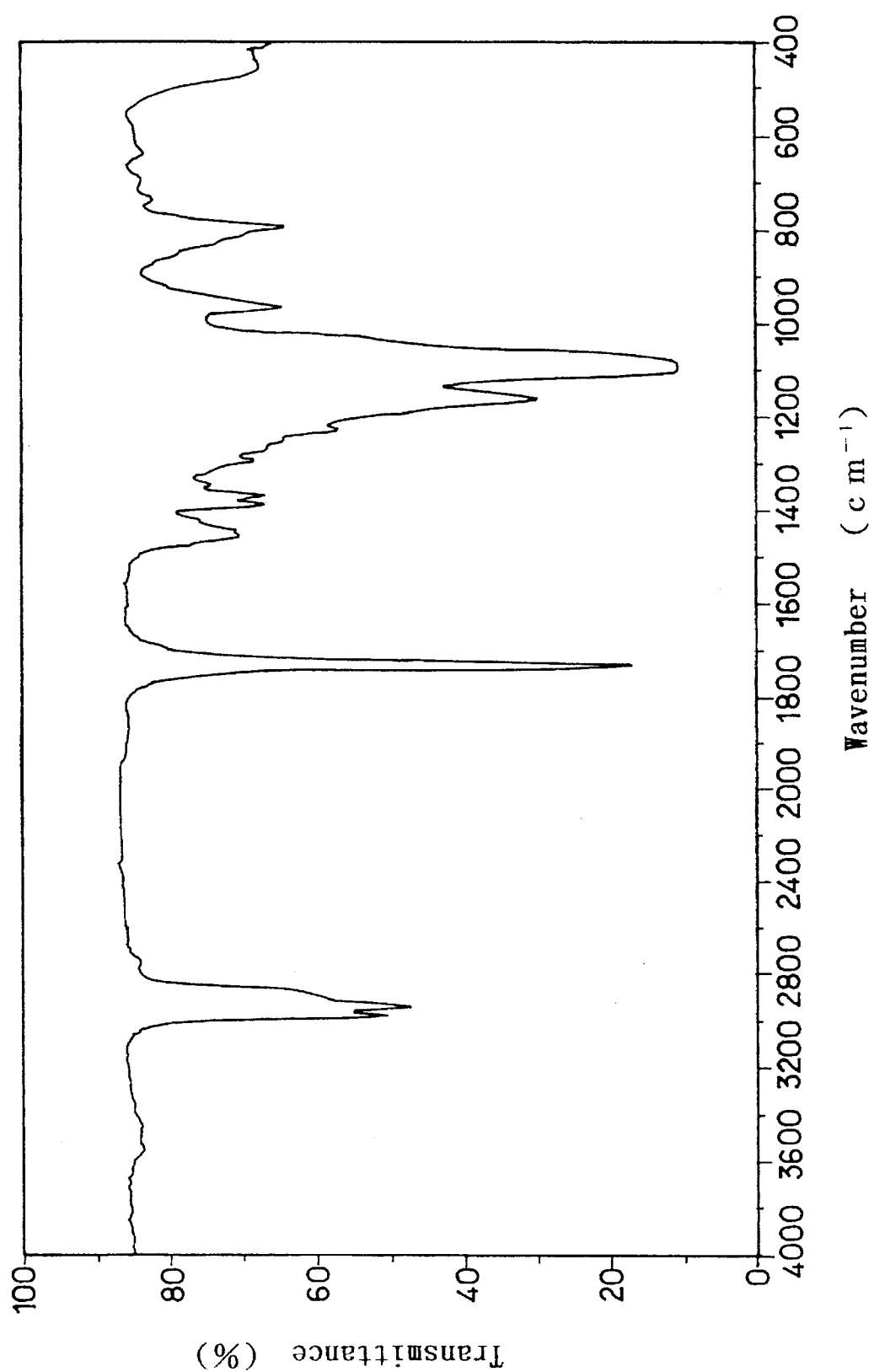
FIG. 1 is an infrared absorption spectrum of the obtained lactone-modified organopolysiloxane compound (i).

Into a 4-necked flask equipped with a condenser, thermometer, nitrogen inlet tube, stirrer, and dropping funnel were placed 744 g of COLCOTE ES 40 and 5 g of n-butyltin trioctate, and the mixture was heated to 140° C. A 228 g quantity (2 mols) of PLACCEL M was added dropwise through a dropping funnel over a period of 1 hour. After 4 hours of stirring, the mixture was cooled, giving a lactone-modified organopolysiloxane compound (ii) according to the present invention. The compound (ii) was a compound of the formula (I) wherein 2 out of an average of 12 ethoxy groups per molecule were substituted by a group represented by

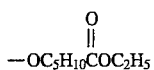

and wherein n is 5. The compound had a number average molecular weight of about 950 as determined by gel permeation chromatography.

Example 3

Preparation of lactone-modified organopolysiloxane compound (iii)

Into a 4-necked flask equipped with a condenser, thermometer, nitrogen inlet tube, stirrer, and dropping funnel were placed 744 g of COLCOTE ES 40 and 5 g of n-butyltin trioctate, and the mixture was heated to 140° C. A 2,052 g quantity (18 mols) of PLACCEL M was added dropwise through a dropping funnel over a period of 10 hours. After 10 hours of stirring, the mixture was cooled, giving a lactone-modified organopolysiloxane compound (iii) according to the present invention. The compound (iii) was a compound of the formula (I) wherein all of an average of 12 ethoxy groups per molecule were substituted by a group represented by

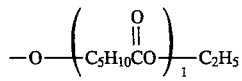

wherein an average value of l is 1.5.

Example 4

Preparation of lactone-modified organopolysiloxane compound (iv)

Into a 4-necked flask equipped with a condenser, thermometer, nitrogen inlet tube, stirrer, and dropping funnel were placed 744 g of COLCOTE ES 40 and 3 g of tetra-n-butoxy titanate, and the mixture was heated to 120° C. A 200 g quantity (2 mols) of δ-valerolactone was added dropwise through a dropping funnel over a period of 4 hours. After 4 hours of stirring, the mixture was cooled, giving a lactone-modified organopolysiloxane compound (iv) according to the present invention. The compound (iv) was a compound of the formula (I) wherein 2 out of an average of 12 ethoxy groups per molecule were substituted by a group represented by

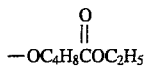

Example 5

Preparation of lactone-modified organopolysiloxane compound (v)

Into a 4-necked flask equipped with a condenser, thermometer, nitrogen inlet tube, stirrer, and dropping funnel were placed 470 g of COLCOTE MS 51 (trademark, product of COLCOTE CO., LTD., a mixture of an average of approximately tetramer of a tetramethyl silicate having an average of about 10 methoxy groups per molecule, the same hereinafter) and 1 g of n-butyltin trioctate, and the mixture was heated to 120° C. A 342 g quantity (3 mols) of PLACCEL M was added dropwise through a dropping funnel over a period of 3 hours. After 2 hours of stirring, the mixture was cooled, giving a lactone-modified organopolysiloxane compound (v) according to the present invention. The compound (v) was a compound of the formula (I) wherein 3 out of an average of 10 methoxy groups per molecule were substituted by a group represented by

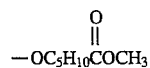

Application Examples 1 to 5 and Comparative Application Examples 1 and 2

Curable resin compositions of Application Examples and Comparative Application Examples were prepared from the lactone-modified organopolysiloxane compounds (i) to (v) obtained in Examples 1 to 5 according to the present invention or from unmodified organopolysiloxane compounds, i.e. COLCOTE ES 40 and COLCOTE MS 51 based on the formulation (calculated as solids) shown in Table 1 by diluting the mixture of the components with xylene to a resin concentration of 50% by weight, calculated as solids.

Each of the obtained curable compositions was applied to a substrate to give a coating film having a thickness of 40 μm when cured. Then, the coated substrate was baked at 140° C. for 30 minutes, giving a test coating film. The obtained coating film was tested for properties by the following methods.

Appearance: A polished mild steel panel was used as a substrate. The coated substrate was inspected to detect the presence or absence of undesirable changes on the coating surface such as delustering, shrinking, cracking, flaking, turbidity, etc.

Gel fraction ratio: A glass panel was used as a substrate. The coating film was peeled off from the glass panel and subjected to extraction by Soxhlet extractor using acetone at a reflux temperature for 6 hours. Thereafter the residue of coating film was measured and expressed in % by weight.

The test results are shown in Table 1.

TABLE 1

| Formulation (on solid basis, part by weight) | Application Example | | | | | Com. Appln. Example | |
|---|---|---|---|---|---|---|---|
| | 1 | 2 | 3 | 4 | 5 | 1 | 2 |
| Hydroxyl-containing resin (1) | 70 | 70 | 60 | 70 | 70 | 70 | 70 |
| Lactone-modified organopoly- | 30 | | | | | | |

TABLE 1-continued

| Formulation (on solid basis, part by weight) | Application Example | | | | | Com. Appln. Example | |
|---|---|---|---|---|---|---|---|
| | 1 | 2 | 3 | 4 | 5 | 1 | 2 |
| siloxane compound (i) | | | | | | | |
| Lactone-modified organopolysiloxane compound (ii) | | 30 | | | | | |
| Lactone-modified organopolysiloxane compound (iii) | | | 40 | | | | |
| Lactone-modified organopolysiloxane compound (iv) | | | | 30 | | | |
| Lactone-modified organopolysiloxane compound (v) | | | | | 30 | | |
| COLCOTE ES 40 | | | | | | 30 | |
| COLCOTE MS 51 | | | | | | | 30 |
| n-Butyltin trioctate | 1 | 1 | 1 | 1 | 1 | 1 | 1 |
| Appearance | Good | Good | Good | Good | Good | Turbid | Turbid |
| Gel fraction ratio | 95 | 94 | 93 | 93 | 95 | 88 | 89 |

What we claim is:

1. A lactone-modified organopolysiloxane compound represented by the formula (I)

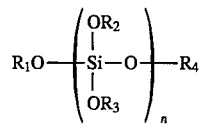

wherein $R_1$, $R_2$, $R_3$ and $R_4$ are the same or different and each represents a methyl group, an ethyl group, a n-propyl group, an isopropyl group or a group represented by the formula

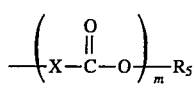

wherein $R_5$ is a methyl group, an ethyl group, a n-propyl group or an isopropyl group, X is a saturated divalent hydrocarbon group having 2 to 14 carbon atoms, and m is an integer of 1 to 3, provided that at least one of $R_1$, $R_2$, $R_3$ and $R_4$ is a group represented by the formula

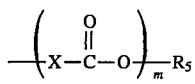

wherein $R_5$, X and m are as defined above, and n is an integer of 1 to 100.

2. The lactone-modified organopolysiloxane compound according to claim 1 wherein at least one of $R_1$, $R_2$, $R_3$ and $R_4$ is a group represented by the formula

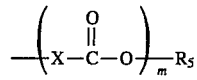

wherein $R_5$, X and m are as defined above and the other is an ethyl group.

3. A process for preparing the lactone-modified organopolysiloxane compound of claim 1, the process comprising subjecting to ring opening addition reaction (i) a silicon compound represented by the formula (II)

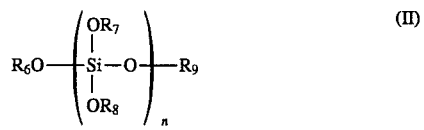

wherein $R_6$, $R_7$, $R_8$ and $R_9$ are the same or different and each is a methyl group, an ethyl group, a n-propyl group or an isopropyl group and n is an integer of 1 to 100, and (ii) a lactone compound represented by the formula (III)

wherein X is a saturated divalent hydrocarbon group having 2 to 14 carbon atoms.

4. The process according to claim 3 wherein the ring opening addition reaction is conducted in the presence of a catalyst for ring opening addition reaction.

* * * * *